(12) United States Patent
Tombs et al.

(10) Patent No.: US 9,486,880 B2
(45) Date of Patent: Nov. 8, 2016

(54) METHOD AND APPARATUS FOR IMPROVING SELECTIVE SOLDERING

(71) Applicant: Pillarhouse International Limited, Chelmsford (GB)

(72) Inventors: Michael Tombs, Leigh-on-Sea (GB); Timothy John Stubbings, Maldon (GB)

(73) Assignee: Pillarhouse International Limited, Chelmsford (GB)

( * ) Notice: Subject to any disclaimer, the term of this patent is extended or adjusted under 35 U.S.C. 154(b) by 0 days.

(21) Appl. No.: 14/430,754

(22) PCT Filed: Sep. 24, 2013

(86) PCT No.: PCT/GB2013/052488
§ 371 (c)(1),
(2) Date: Mar. 24, 2015

(87) PCT Pub. No.: WO2014/049340
PCT Pub. Date: Apr. 3, 2014

(65) Prior Publication Data
US 2015/0273634 A1    Oct. 1, 2015

(30) Foreign Application Priority Data
Sep. 25, 2012 (GB) .................................. 1217069.2

(51) Int. Cl.
*B23K 31/02* (2006.01)
*B23K 31/12* (2006.01)
(Continued)

(52) U.S. Cl.
CPC ............. *B23K 31/12* (2013.01); *B23K 1/00* (2013.01); *B23K 1/0016* (2013.01); *B23K 1/08* (2013.01); *B23K 1/20* (2013.01); *B23K 3/0607* (2013.01);
(Continued)

(58) Field of Classification Search
None
See application file for complete search history.

(56) References Cited

U.S. PATENT DOCUMENTS 4,877,175 A * 10/1989 Jones .................... B23K 1/018
219/121.65
5,304,256 A * 4/1994 Showalter ................ B23K 7/06
148/202
(Continued)

FOREIGN PATENT DOCUMENTS

CN    201685000 U    12/2010
DE    3001852 B1    11/1980
(Continued)

OTHER PUBLICATIONS

Machine translation of JP-10193092A (no date available).*

*Primary Examiner* — Kiley Stoner
(74) *Attorney, Agent, or Firm* — Blank Rome LLP

(57) ABSTRACT

A method of assessing discrepancy between a target value and a measured value of a parameter of contact area produced between flow of solder ejected from a nozzle and a surface is defined in the present application. This method comprises the steps of: providing a surface of material through which contact area between solder ejected from a nozzle and a side of the surface can be visually detected, for example using a camera; flowing solder through a nozzle and then bringing the solder into contact with a side of the surface, thereby creating contact area between the solder and said side of the surface; detecting the contact area from the other side of the surface so that a value of a parameter of said contact area can then be measured; and assessing any discrepancy between the target value and the measured value so that any necessary compensation in order to achieve the target value can be programmed.

13 Claims, 13 Drawing Sheets

(51) Int. Cl.
  *B23K 1/00* (2006.01)
  *B23K 1/08* (2006.01)
  *B23K 1/20* (2006.01)
  *H05K 3/34* (2006.01)
  *B23K 3/06* (2006.01)
  *B23K 3/08* (2006.01)
  *B23K 37/06* (2006.01)
  *G01N 13/02* (2006.01)
  *H05K 1/02* (2006.01)
  *H05K 3/00* (2006.01)

(52) U.S. Cl.
  CPC ............... *B23K 3/08* (2013.01); *B23K 37/06* (2013.01); *H05K 3/34* (2013.01); *H05K 3/3468* (2013.01); *B23K 2201/42* (2013.01); *G01N 13/02* (2013.01); *H05K 1/0269* (2013.01); *H05K 3/0008* (2013.01); *H05K 2203/0126* (2013.01); *H05K 2203/04* (2013.01); *H05K 2203/163* (2013.01)

(56) References Cited

U.S. PATENT DOCUMENTS

| | | | |
|---|---|---|---|
| 5,388,468 A | 2/1995 | Sasson | |
| 5,533,663 A * | 7/1996 | Massini, Jr. | B23K 3/0653 228/103 |
| 5,538,175 A * | 7/1996 | Massini, Jr. | B23K 3/0653 228/102 |
| 5,767,424 A | 6/1998 | Breunsbach et al. | |
| 5,979,740 A | 11/1999 | Rooks | |
| 6,085,960 A | 7/2000 | Kim et al. | |
| 6,119,915 A | 9/2000 | Thompson, Sr. | |
| 6,510,724 B1 * | 1/2003 | Weiss | G01N 3/00 73/1.01 |
| 7,797,069 B2 * | 9/2010 | Silverbrook | B22F 3/008 228/180.21 |
| 2002/0036223 A1 * | 3/2002 | Saito | B23K 3/0653 228/37 |
| 2008/0156990 A1 * | 7/2008 | Ohashi | G01N 21/276 250/341.1 |
| 2009/0122306 A1 * | 5/2009 | Ohashi | G01N 21/95684 356/237.5 |
| 2010/0021050 A1 * | 1/2010 | Kakuda | B23K 1/0016 382/150 |
| 2016/0031044 A1 * | 2/2016 | Marino | B23K 31/12 228/102 |

FOREIGN PATENT DOCUMENTS

| | | | |
|---|---|---|---|
| DE | 195 05 763 A1 | 9/1995 | |
| DE | 20 2006 009 139 U1 | 10/2006 | |
| JP | S 61-95768 A | 5/1986 | |
| JP | 62267065 A * | 11/1987 | |
| JP | 1-205593 A | 8/1989 | |
| JP | 02-6163 | 1/1990 | |
| JP | H 05200540 A | 8/1993 | |
| JP | H 09-5012 A | 1/1997 | |
| JP | 10153473 A * | 6/1998 | |
| JP | 10-193092 A | 7/1998 | |
| JP | 11340621 A * | 12/1999 | |
| JP | 2000-5868 A | 1/2000 | |
| JP | 2000-244107 A | 9/2000 | |
| JP | WO 2010131752 A1 * | 11/2010 | ........... B23K 3/0653 |
| WO | WO 2010/131752 A1 | 11/2010 | |
| WO | WO 2013/111651 A1 | 8/2013 | |

* cited by examiner

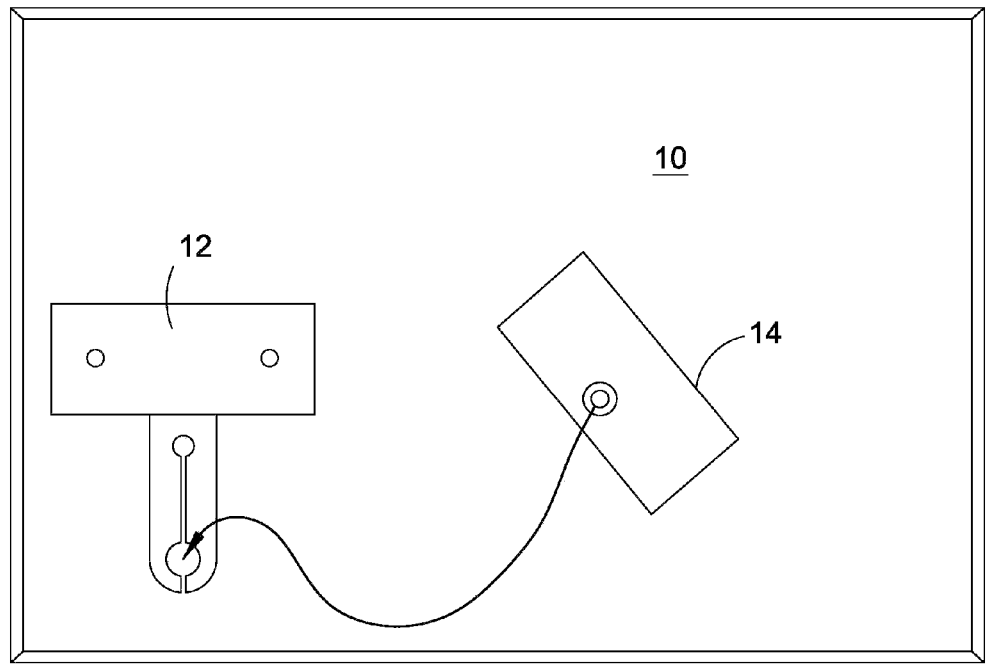
Fig. 11
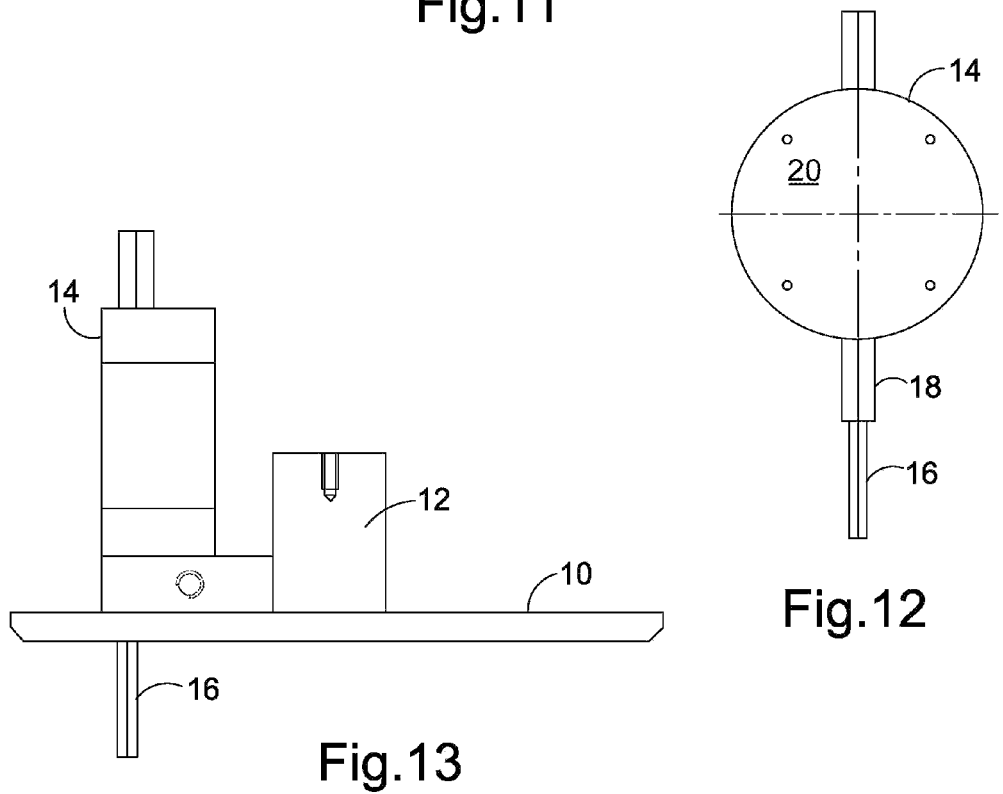
Fig. 12
Fig. 13

METHOD AND APPARATUS FOR IMPROVING SELECTIVE SOLDERING

The present invention relates to a method and apparatus for improving or optimising the precision and/or accuracy of soldering operations, and preferably selective soldering operations. In particular, the present invention relates to measurement and calibration methods for improving or confirming the precision or repeatability of a soldering operation or for detecting mal-alignments or other non optimised operations from a nozzle, or other nozzle faults, and to an apparatus for performing such measurement, detection, improvement, optimisation and calibration methods.

In selective soldering applications, printed circuit boards (PCBs) are handled on or within a soldering apparatus for soldering components onto the PCBs. For this the PCBs are often handled through automated processes employing robots or other automatic machines. In other arrangements, however, the PCBs are loaded manually into the apparatus onto a PCB workstation and then processed on the PCB workstation by the soldering apparatus before being manually removed from the PCB workstation. That workstation may be moveable within the soldering apparatus, or it may be fixed in a particular position within the soldering apparatus.

Usually the soldering occurs by moving a soldering nozzle into a position below the PCB for applying a solder flow to the underside of the PCB, thus applying solder to a component on the PCB for connecting it thereto.

The soldering processes, especially selective soldering processes, must be sufficiently precise in order to avoid damage to the PCBs and their components, or of other components or devices on the PCBs. Further, the processes must remain precise through numerous sequential processes since often a soldering apparatus is used to produce multiple identical PCBs, i.e. on repeat runs. This repeatability is thus to maintain consistent results.

There is a demand of performing soldering operations at increased precision, accuracy and speed, or with increased long term repeatability, or with less need for manual tuning during such repeat runs, while still ensuring precision, accuracy, speed or repeatability.

PCBs and the processes for soldering components thereon are typically designed so that the soldering of the components is carried out from the underside of the PCB. Some PCBs are even double sided, whereby they may need to be turned over once one side is soldered. Typically, therefore, both sides are still soldered from the underside.

One way of soldering PCB components from the underside is that of providing a flow of molten solder as a "bubble" or generally circular overflow flowing from a soldering nozzle. A typical bubble is a circle from above, and approximately a hemisphere from the side (or a cone with a hemispherical top, or similar). This bubble is moved towards the PCBs for the soldering, or vice versa. Jet and wave soldering techniques are also known in the art, e.g. where a jet or wave (line) of solder is passed under the PCB, e.g. for soldering an array of component terminals at a time. The present invention is equally applicable to such techniques since again precision and repeatability has its benefits.

The present invention therefore provides a method and apparatus for improving or optimising the precision and/or accuracy of soldering operations, and preferably selective soldering operations. In particular, the present invention relates to measurement and calibration methods for improving or confirming the precision or repeatability of a soldering operation or for detecting mal-alignments or other non optimised operations from a nozzle, or other nozzle faults, and to an apparatus for performing such measurement, detection, improvement, optimisation and calibration methods. Typically these methods are carried out, and corrected where necessary, automatically, e.g. by robotics or automated drivers provided on the soldering apparatus or nozzle assembly. Manual optimisation and calibration is also possible, and can be preferred so as to reduce the complexity or cost of the equipment required.

Preferably the system is incorporated directly into the soldering apparatus, although the nozzle characteristics may be detected or checked by the method on an assembly separate from the soldering apparatus whereupon the nozzle assembly, when incorporated into the soldering apparatus (either manually or automatically), will have pre-known bubble, jet or wave performance characteristics, whereby the driver for the PCB or nozzle assembly can be correctly calibrated therefor.

Preferably the method of the present invention provides for calibration or adjustment or optimisation of nozzles or assemblies for spot-type soldering or single point, single line or single region soldering, e.g. for nozzles for soldering only a single area, spot, line or region of the PCB with the bubble, jet or wave at any given point in time. Apparatus using multi strip, multi bubble, multi wave, multi jet and multi spot nozzle arrangements are also anticipated for use with the present invention, each nozzle or solder outlet potentially utilising a separate parameter check or alignment process.

The process of soldering components onto a PCB with such soldering apparatuses is generally very quick, as the hot, liquid solder almost instantaneously joins the component to the PCB and to the circuit track of the PCB. Once the solder is applied, the soldering nozzle is then usually moved relative to the PCB, usually downwardly in the z direction and then in an X-Y plane (that is a horizontal direction, and typically parallel to the plane of the PCB). This is so that it can reach either the next spot or area to be soldered or a holding/stowage position (e.g. if the PCB is then to be removed from the apparatus, or otherwise moved thereon or therein (e.g. for turning it over).

In typical applications, the hot, liquid, running solder flows out of an outlet of the nozzle in an upwards direction to form the bubble in which terminations to be soldered are immersed. The size of the bubble affects the precision and/or accuracy of the soldering, and some applications demand smaller bubble sizes to be used, e.g. where delicate or small components are to be attached to the PCB. Other applications instead have the flow in a sideways or angled direction, e.g. for wave or jet soldering techniques.

Rapid and accurate application of the solder is particularly desired where electronic components tend to be smaller. This is since smaller components typically heat up quicker, and it is often damaging to overheat the components. Such demands can lead to the provision of smaller nozzles, e.g. since they offer a smaller heat mass. With a smaller nozzle, however, the accuracy of application required is increased since erroneous alignments, such as inaccurate vertical or sideways positioning, e.g. positioning thereof with displacements from an optimum position, can quickly take the bubble or wave or jet away from a workable or efficient soldering position. For example, nozzle tip diameters of 1.5 mm are possible (this is the diameter of the opening of the nozzle), although this is currently considered to be amongst the smallest possible nozzles in order to achieve satisfactory soldering processes since any smaller and the nozzles will tend to freeze due to their low heat mass or low thermal flow volume. Thus only a small error can lead to ineffective soldering.

Even the larger, more conventional nozzles can easily be non-optimally located for soldering simply by having only small locating errors relative to the PCB/components.

It is also observed that with the smaller nozzles, the shape and size of the solder bubbles formed from such small solder tips can vary slightly (but significantly given the size) from one tip to the next (e.g. upon tip replacement, or from one machine to the next). As such it is difficult both to characterise (i.e. predict) the bubble performance and to reproduce soldering results consistently and accurately across multiple machines/nozzles without first witnessing the bubble characteristics. As a result, such machines typically need individual, careful adjustment before commencing soldering operations. It will be appreciated therefore that the advantages that are brought about by use of a narrow nozzle outlet (and thus a smaller bubble), in terms of achieving soldering of smaller components, or soldering into tighter locations, can be ultimately offset by the disadvantages caused by an increased level of individual setting up, or else the resulting lack of reproducibility of the contact between the bubble, wave or jet and the PCB between machines and nozzles. Thus, a higher soldering accuracy cannot always be achieved just by narrowing the solder nozzle's outlet.

The shape of the contact area between the bubble and the PCB is a parameter that depends on several factors in addition to the size of the nozzle tip from which the solder is made to flow. Amongst these additional parameters there are the distance between the nozzle and the PCB, the speed of exit of the solder from the nozzle tip, the local geometry of the contact area between the bubble, the to-be-soldered terminations and the PCB, and use and ageing of the soldering apparatus. With the present invention, upon detecting these parameters, adjustments can be made to provide consistent results from varying nozzle arrangements.

Since there is a strong interest in the industry to be able to perform the soldering operations at increasing speeds and at an increased level of accuracy and efficiency, software-controlled robots or other automated machines are increasingly being incorporated into soldering apparatus. This is beneficial since the trajectory of the soldering nozzle, the time spent at each soldering location and the registration or location of the soldering nozzle relative to the PCB are all examples of parameters that can be numerically controlled by software-controlled robots or other automated machines on the soldering apparatus. These robots and machines can thus now be utilised by the present invention to help implement the present invention's error correction capabilities.

When soldering nozzles of this type are made to travel at high speeds, or through frequent accelerations, the positioning of the nozzle at the time of application of the molten solder on the target location can be inaccurate if the movements/accelerations are too fast. These kinds of inaccuracies are typically caused by the mechanical infrastructure that moves the soldering nozzle, or simply by the accelerational forces therefrom, and they can cause rippling or displacement of the solder bubble away from the predicted or expected location at a given point in time. For example, the mechanical infrastructure is subject to mechanical tolerances, mechanical vibrations, use and ageing, change of lubrication conditions etc and these factors can ultimately affect the precision and/or accuracy of the selective soldering operations because they affect the reproducibility of the trajectories and positions of registration of the soldering nozzle, or the bubble therefrom, and potentially also the reaction of the bubble, jet or wave to the accelerations or movements prior to or at the time of the soldering operation. With the present invention, these inaccuracies can also be determined and compensated for, thus further improving repeatability or accuracy of the soldering process.

Other phenomena, more or less transient, can also affect the precision and accuracy of selective soldering operations, such as "dewetting", "freezing", "jetting" and "bobbling". "Dewetting" is caused by an imperfect flow of the return film of solder along a section of the nozzle, i.e. where the visual appearance of the solder flow is turbulent. This is typically as a result of damage or wear to the nozzle. A vertical shift of the bubble ("bobbling") is also possible, and it will generally be unpredictable and is certainly undesirable due to the lack of symmetry or precision that generally results. It can result from damage to the solder pump, or due to accelerations by the machine (for whatever reason). "Freezing" is the result of a complete or partial obstruction of the soldering nozzle, or due to the molten solder cooling within the flow-path, and it is usually manifested as a solidification of the solder flow due to a drop in the temperature of the molten solder at the nozzle's outlet, or within the bubble upon contact with the component/PCB. It is thus typically a result of a rapid temperature drop in the solder within the bubble (such as due to a temperature difference between the termination and the solder bubble). Preheating typically assists in minimising the occurrence of this phenomenon, and other approaches are also known, such as increasing solder flow rates or nozzle sizes, or by providing optimised nozzle designs for small nozzle applications, such as vented nozzles. Nevertheless, freezing can still occur unexpectedly. "Jetting" refers to an uncontrolled detachment of the solder bubble from the nozzle tip. This can result from the above-mentioned increased flow rates, or dewetting. The present invention can also be used to detect these phenomenon.

It is clear that of all the potential variables that can affect the precision and/or accuracy of selective soldering, some can only be partially controlled, and some cannot be controlled. In addition, certain variables may even be unknown to the user of the selective soldering procedure, and as such will be more problematic to deal with in case of unsatisfactory performance. Identifying the problem, however, allows corrections to be made, be that replacement of the nozzle, or adjustment of the parameters of the nozzle or the solder flow.

The present invention therefore serves to enable an increase in the precision or accuracy or repeatability of soldering processes by looking to solve or identify the occurrence of at least one of the above-mentioned problems.

The present invention, in one aspect, establishes testing procedures that allow the above-described phenomena to be observed, measured, evaluated or countered/corrected, so that the performance of the soldering nozzle against the PCB/component can ultimately be optimised or otherwise characterised in terms of its reproducibility, accuracy, form, size and/or shape etc . . .

The present invention in another aspect also provides a testing routine, and/or calibration procedure, that enables a more accurate and fast characterisation or optimisation of the performance of a soldering nozzle relative to a PCB or component under existing conditions, which conditions may vary from time to time, or over time, e.g. due to wear or replacement of interrelated components of the soldering apparatus.

The invention provides a method of observing, determining or measuring a parameter of a contact area produced between a flow of solder ejected from a soldering nozzle and a surface, the method comprising the steps of:

providing the surface on a sheet of material through which the contact area can be visually detected;

flowing the solder through the soldering nozzle;

bringing the flow of solder into contact with the surface, thereby creating the contact area between the flow of solder and said surface; and observing the contact area from the other side of the sheet of material.

Preferably the method further comprises measuring one or more parameter of said contact area.

The invention also provides a method of assessing discrepancy between a target value and a measured value of a parameter of contact area produced between flow of solder ejected from a nozzle and a surface comprises the steps of: providing a surface of material through which contact area between solder ejected from a nozzle and a side of the surface can be visually detected, for example using a camera; flowing solder through a nozzle and then bringing the solder into contact with a side of the surface, thereby creating contact area between the solder and said side of the surface; detecting the contact area from the other side of the surface so that a value of a parameter of said contact area can then be measured; and assessing any discrepancy between the target value and the measured value so that any necessary compensation in order to achieve the target value can be programmed.

Preferably the present invention provides a method of measuring a parameter of a contact area produced between a flow of solder ejected from a soldering nozzle and a surface, the method comprising the steps of:

providing the surface on a sheet of material through which the contact area can be visually detected;

flowing the solder through the soldering nozzle;

bringing the flow of solder into contact with the surface, thereby creating the contact area between the flow of solder and said surface;

detecting the contact area from the other side of the sheet of material; and measuring one or more parameter of said contact area.

Preferably a measured parameter is one or more of a size or length, e.g. the splash-length or splash-width or splash-diameter, a position of the splash relative to a predetermined marker, or a shape of the splash.

Having measured the parameter, that parameter can be compared against a stored value, or a desired value, or threshold values, whereby deviations therefrom can be detected or determined.

If a deviation is detected or determined, or if the deviation exceeds a given threshold, the method can then further attempt to correct the defect. For example, relative positions of the nozzle or sheet can be adjusted, or the solder flow rate can be adjusted. This can then hopefully correct the deviation or adjust the parameter.

Preferably the nozzle position can be adjusted to correct the deviation, e.g. by raising or lowering it respectively to increase or reduce the size of the contact area (the splash), or by moving the nozzle laterally to move the contact area into a position where the splash more correctly aligns with the marker.

Preferably the parameter is measured relative to one or more optimised marker on the sheet, those markers defining optimal splash positions or optimal splash shapes or optimised splash sizes, or threshold values therefor. For example, if the determined parameter falls within the range defined by upper and lower thresholds, a measured parameter can be determined to be acceptable.

If it is determined, however, that the deviations are such that they are non-correctable, e.g. if the shape of the splash is wrong, it may be determined that the nozzle has failed or is otherwise damaged, e.g. it may be exhibiting the characteristics of "dewetting", "freezing", "jetting" or "bobbling". In this circumstance, the method may issue a warning to the operator (e.g. an audible or visual flag), whereupon the nozzle can be replaced, or the machine can be serviced (e.g. the pump replaced). The testing/calibration process can then be commenced again.

Using the present invention, for any given nozzle, or at any given time in the life of a nozzle, allows a position of the nozzle relative to an underside of a PCB to be optimised or checked—the surface of the sheet used by the method represents the underside of the PCB. By having an optimised contact area or splash on the sheet of material, for example achieved by fine tuning the flow of solder, or the position of the nozzle, that same contact area can be repeated on the PCB. Further, that same contact area, or one having acceptable similarities, i.e. one falling within acceptable tolerances, can be repeated from one nozzle to the next, and also it can be checked and corrected where needed, from one time to the next, thus allowing consistent and repeatable soldering processes to be carried out.

Preferably the solder is illuminated to assist the observation of the contact area. Preferably the illumination is from above the sheet of material, and preferably the illumination is by a lightbox, with the observation being undertaken through the lightbox.

Preferably the contact area is magnified to assist the observation of the contact area.

Preferably the soldering nozzle has an internal diameter of less than 4 mm. More preferably it has an internal diameter of less than 2 mm. Diameter typically applies to round outlet diameters, although the outlets may be non round, whereby instead of a diameter, it is the largest diametrical dimension that should be less than 4 mm or preferably less than 2 mm. Larger sizes, however, can also benefit from the present invention's method.

Preferably an image of the contact area is captured by a camera. Typically the camera is located above the sheet of material.

It is preferred that the solder is arranged to contact the sheet of material for no more than 4 seconds before the flow of solder is brought out of contact with the surface. This is to avoid excessive heating of the sheet of material. Due to this short contact period, the image is usually the observed record of the contact area, with the parameters being determined from that image.

It will be appreciated that the present invention also provides a method of assessing for any discrepancy between a target value and a measured value of a parameter of a contact area produced between a flow of solder ejected from a soldering nozzle and a surface, the method comprising the steps of:

measuring a value of the parameter of the contact area produced between the flow of solder ejected from the soldering nozzle and the surface using the method defined above; and assessing for any discrepancy between the target value and the measured value.

The present invention also provides a method of calibrating a contact area produced between a flow of solder ejected from a soldering nozzle and a surface, the method comprising the steps of:

assessing for any discrepancy between a target value and a measured value of a parameter of a contact area produced between a flow of solder ejected from a soldering nozzle and a surface using the method defined above; and reducing said discrepancy by one or more of the following actions:

changing the speed of a solder pump;

adjusting the relative location of the solder nozzle in the X direction;

adjusting the relative location of the solder nozzle in the Y direction; and adjusting the relative location of the solder nozzle in the Z direction.

The present invention also provides an apparatus configured for performing any one of the methods defined above, said apparatus comprising:

means for visually detecting a solder contact area on a sheet of material from a side of the material opposite to that contact area; and means for measuring a parameter of said detected solder contact area.

The apparatus may be incorporated into a soldering apparatus, e.g. at a soldering optimisation station, or simply as part of a PCB workstation.

The soldering apparatus may comprise a PCB workstation that can be lifted or dropped relative to a soldering nozzle. Alternatively or additionally the soldering apparatus may comprise a soldering nozzle that can be lifted or dropped relative to a PCB workstation.

Preferably the nozzle or PCB workstation, or both, can be moved forwards and/or sideways, and/or rotated or pivoted, relative to the other.

Preferably the apparatus within the soldering apparatus is used by placing the sheet of material on a PCB workstation within the soldering apparatus, with the means for visually detecting a solder contact area on the sheet of material from a side of the material opposite to that contact area, and the means for measuring a parameter of said detected solder contact area, being both arranged above the PCB workstation when the method of the invention is being carried out. Those means may be permanently in such a position or may be displaceable into such positions.

In another arrangement, the apparatus within the soldering apparatus is used when the soldering nozzle is located in a parked, holding or stowage location, preferably away from (e.g. not directly underneath) the soldering apparatus' PCB workstation.

Preferably the means for visually detecting a solder contact area on the sheet of material from a side of the material opposite to that contact area, and the means for measuring a parameter of said detected solder contact area, are both arranged above the nozzle's parked, holding or stowage location when the method of the invention is being carried out. Those means may be permanently in such a position. Alternatively they may be displaceable into such a position.

Preferably the apparatus comprises two cameras, one for carrying out an observation of the contact area and the other being on a carriage for the nozzle. Preferably the other camera is for carrying out solder nozzle guidance or solder nozzle location checks.

Preferably the markers comprise one or more of a crosshair, a circle, a pair of circles, marker dots.

The markers may be electronic or virtual markers, e.g. markers that are superimposed electronically onto the sheet.

For jet applications, the markers preferably comprise one or more ovals.

For wave applications, the markers preferably comprise one or more elongated ovals with substantially straight longer sides, or rectangles.

The invention also provides a method for determining the height of a nozzle's tip below a PCB workstation in a soldering apparatus, comprising the steps of providing on the PCB workstation a plate carrying a vertical displacement measuring apparatus, the end of which has a known position relative to the underside of the plate, engaging the tip of the nozzle against the end of the vertical displacement measuring apparatus, determining the vertical displacement of the end resulting from the engagement, and calculating the vertical distance between the underside of the plate and the tip of the nozzle.

Preferably the vertical displacement measuring apparatus is a clock.

Preferably the vertical displacement measuring apparatus is a digital clock.

The present invention also provides a method for calibrating a positional control system for a soldering nozzle in a soldering apparatus, the method comprising providing a test plate within the soldering apparatus at a PCB workstation thereof, the test plate having a portion thereon that is able to be marked by a contact area of a solder flow, moving the soldering nozzle, with a solder flow passing therethrough, using the positional control system, such that the solder flow moves into engagement with the underside of portion of the test plate at a first position to make a mark thereon, the movement being to target a particular position of that underside, checking the location of the mark, comparing the actual position with the intended position and correcting, where necessary, the calibration of the positional control system in the x or y axes so as to correct for any discrepency between the actual position and the intended position.

Preferably the portion is provided by a test paper.

Preferably the portion is in the form of a sticker.

Preferably the portion is made from a thermal paper. As such the mark is a darkening of the paper. A lightening of the portion at the mark, or some other form of mark creation such as by way of a dissolvable portion, or a removeable primer, such as chalk are also considered to be possible embodiments. For example, it is possible to use an ink printed label, with the label being made of a plastic material, or some other material from which the ink can be removed, with the ink being a soluble or non-permanent ink such as an alcohol or water based ink, and then when the solder touches this type of ink, the ink is washed away to leave a mark—the mark being the label background. Further, fiducial or other graphical marks may be printed onto the label and these can be used to test the programme as the software can correct to the fiducial or graphical marks.

Preferably the portion is marked for defining target locations.

Preferably the portion is marked with graduations for assisting to determine any discrepencies.

Preferably the plate additionally has measurement markers for calibrating the carriage control across substantially the full width or height of working area of the PCB workstation, the measurement markers being ruler marking extending along substantially the full width or height of the test plate., Preferably the test plate has two target areas for the calibration, a first for a first solder flow application, or a first set of solder flow applications, and a second for a second solder flow application, or a second set of solder flow applications, the method involving providing the first mark in the first part of the process, and the second target area being for checking the calibration after an adjustment has been made.

Preferably the method also includes checking the size of the mark to verify that the contact area is also within predetermined tolerances of a particular intended soldering job.

These and other features of the present invention can be used in isolation or in combination.

The present invention will now be described, purely by way of example, with reference to the accompanying drawings, in which:

FIGS. 11 to 13 show a device used for obtaining a manual datum level for the soldering nozzle with respect to an underside of a PCB workstation.

Figure 1:
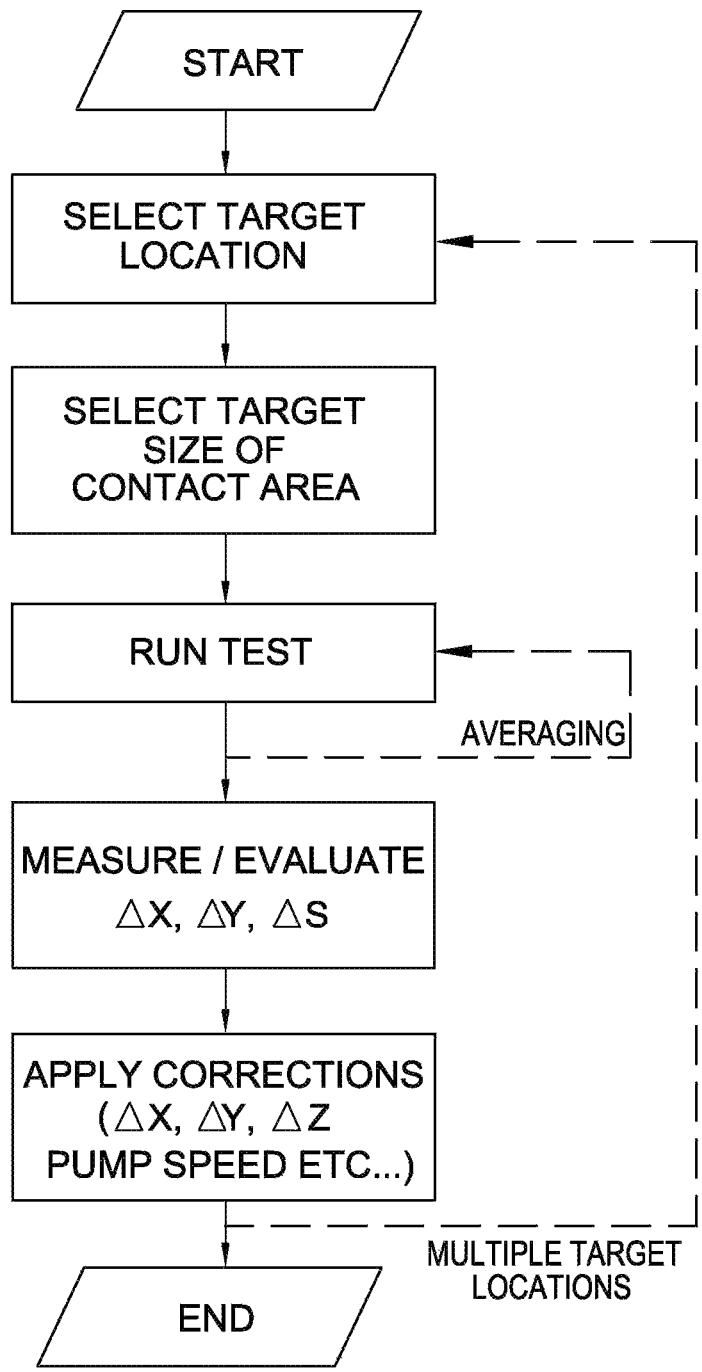
FIG. 1 is a flow chart representing a calibration routine for soldering applications based on the present invention.

The present invention utilises a testing process to verify or optimise the contact area of a solder flow during PCB soldering operations by having the solder flow operate against an underside of a sheet of material through which the contact area can be detected.

A camera system has been developed for detecting the size of the contact area of the solder flowing from a soldering nozzle when the nozzle is brought in proximity of the underside surface.

The system may use a light to illuminate the solder, e.g. to enhance the contrast between the solder and the background—molten solder, after all, is highly reflective, and thus can be difficult to pick-up on a video image. The light may be a ring light, but more preferably the illumination is achieved using a light box, i.e. a prismatic light source, allowing the camera to look directly down on the solder, through the sheet of material, and yet also to have the light source passing through the visual axis of the camera. The light may be a sidelight redirected along that axis by a prism.

The system can be computerised or simply visualised on a computer, and the images acquired by the camera can be recorded by software and can be post-processed or analysed as necessary, thus allowing a user, or the computer, to correct or change parameters of the solder flow, or the nozzle, to optimise the contact area.

The flowing nozzle is brought up along coordinate Z (vertical direction) until the solder contacts the sheet, which is typically a horizontally supported plate made of a suitable glass. The camera looks down from above to detect the size or shape, or some other parameter of the contact area of flowing solder on the glass. The images are captured by software and are visualised on a screen. The nozzle may then be retracted from the glass to avoid overheating the glass. Typically the nozzle is flowing solder against the glass for no more than 4 seconds, and potentially less than a second. Further, in the preferred arrangement the computer displays a screen with a first image—the live or working image (thus showing the approaching flow of solder), and a second image—a recorded or stored image. The live or working image is typically a live image as the nozzle approaches the glass, and is then a captured image once the nozzle starts to reverse away from the glass, thus providing a snap-shot of the maximum contact area until a command is entered to start the nozzle's approach again—the retraction is thus not visualised. The second image is the recorded image, e.g. from a previous test run, and updates when a test run image is saved.

The software is programmed so that two rings are visualised or superimposed on the plane of the glass surface. The circles represent minimum and maximum boundaries, i.e. thresholds, that are allowable for the contact area, i.e. for a predetermined registration location of the nozzle with respect to a coordinate system fixed with the plane of the glass ($X_{reg}$, $Y_{reg}$ and $Z_{reg}$). In other words, the circles represent a target size and position for the solder contact area. Shapes and target forms other than circles, such as cross-hairs, squares and rectangles, or even triangles, or other polygons, are also envisaged.

The target size can be inputted via the software, or can be printed on the glass, but by having it electronically superimposed it can easily be changed as desired, e.g. for different soldering applications.

With the controls provided by the software, it is possible to adjust the position, and to centre, the visualised contact area within the circles as desired, by making adjustments in the X and Y directions. This is usually done for the snap-shot on the live feed, and can be automated. Further, by adjusting the height of the soldering nozzle in the Z direction or more likely the height of the bubble by altering the pump speed, it is possible to adjust the size of the contact area of the solder. This also can be automated. However, both are preferably manually done to keep equipment costs and processing requirements to a minimum.

Adjusting the pump speed is the preferred method for adjusting the solder height and thus for controlling or adjusting the size of the contact area. This is since it is generally critical for the soldering process for the nozzle's height never to exceed a certain level—it must not be too close to the PCB, for example, due to the leg length of the terminals of the components extending below the PCB. If you get too close you can start to close off the flow path for the solder, whereupon the solder can squirt or freeze or flood the PCB—the leg may for example penetrate into the top of the nozzle!

Once an adjustment for the contact area of the solder has been made in the X and Y directions, and once the adjustment for the size of the contact area has also been made, so as hopefully to bring it within the target (all either by acting on the corresponding software controls, or by automated processes), and once the user is satisfied with the adjustments it is possible to save the relevant data to the computer using the "Write Log" button of the program. A new registration position for the soldering nozzle has therefore been determined ($X_{reg}'$, $Y_{reg}'$ and $Z_{reg}'$) and is ready for use in the soldering operations.

Instead of trying to correct all parameters in one go, however, sequential steps may be appropriate, i.e. first correcting the x direction, then correcting the y direction and then correcting the z direction.

Further test runs can also be carried out to verify adjustments—useful since the adjustments are not made to a live feed, but to a snap shot, and as such may not be entirely reliable—the snap-shot may be a skewed bubble for example.

Periodically, or when the user is dissatisfied with the outcome of the soldering operations, for example when the user detects PCBs that have not been soldered within predetermined accuracy, the user can go back and use the system to check whether that the nozzle is still running correctly, i.e. whether the nozzle is still registering correctly at ($X_{reg}'$, $Y_{reg}'$ and $Z_{reg}'$). If so, he can then check that the size of solder contact area is still satisfactory. If the registration location and/or size of contact area are not satisfactory the user will use the system to recalibrate the nozzle. Alternatively, he will change to a new nozzle, especially if the contact area has an unexpected shape.

Typically when a new nozzle is installed, optimal flow characteristics are restored, which means that any adjustments made to the nozzle position or solder flow rates to correct for wear may cause non-optimal contact area performance. As such, the method or program will show performance is wrong until the system is reset to original parameters ($X_{reg}$, $Y_{reg}$ and $Z_{reg}$). Alternatively, the new nozzle may have its own unique characteristics, whereby adjustment is again needed.

Adjustments to the solder contact area can be implemented by changing the pump performance or speed, e.g. by adjusting the rotational speed of the pump impeller, thus changing the flow rate of the solder.

The system described above has application to multiple nozzle sizes, but is very useful for optimising nozzle control for nozzles that have a small diameter due to their requirement for high positional accuracy under a PCB. As such, the present invention has particular use for small nozzles such as those having an outlet diameter of less than 4 mm, and best for those with an outlet diameter of around 1.5 mm.

The process described above can be supervised by the user, or can be made automatic.

The provision of two rings on the glass is optional, in that there might just be one, or even three, with the rings purely being there to define the target contact area or a range of acceptable contact areas so as to allow the adjustment of the board height relative to the nozzle to optimise the contact area. Likewise, cross hairs can be present on the screen visualised by the user to help with determining the X and Y coordinates of the target or the actual position of the contact area with respect to X/Y centres. These lines therefore assist with centralisation.

Some software applications can use just a circle. Others may just use a calibrated cross hair. Yet others may just use two, three or four (or more) dots defining points for aligning on the edge of the contact area. Any such marks might be adequate to allow a user to check the contact area against optimisation parameters.

For bubble solder flows, there is typically a substantially circular contact area, and substantial edge irregularities typically suggest that there is a problem with the nozzle or the solder flow rate. Other nozzle arrangements are characterised by different contact area shapes, e.g. oval or elongated ovals with substantially straight sides.

The rings or cross hair are preferred to be programmable, and they are programmable in the illustrated example in that the user can change their size to suit the nozzle size, or the required contact area. In other words, the target parameters can be user-defined. The rings and cross hair are superimposed electronically by the software, i.e. they are virtual.

In other arrangements, the markers might be changeable through the provision of interchangeable glass plates, or changeable target areas, e.g. with rotatable or slidable glass screens with different markers provided on different areas thereof.

Further examples of the present invention are now described further with reference to the drawings.

With reference to FIG. 1 of the drawings, a calibration routine for improving the performance of selective soldering operations is illustrated by means of a flow chart. The user initially selects a target location, i.e. a target soldering spot on the board that requires scrutiny by using the system, for example because non optimal soldering has been detected at that location. A target size of solder contact area is associated by the user with the target location—this may depend on the type of electric component and terminals to be soldered at that location. These parameters could alternatively be stored in the program that controls the system. The target size of solder contact area is the desired or target parameter.

The user then "runs a test", i.e. asks the system to bring the soldering nozzle in the selected target location and by means of the camera the system can detect, acquire, measure, analyse etc . . . , as required, raw data. The data represent the actual solder contact area detected through the glass in the test run.

The test can be repeated if averaging is required.

By a comparison between the target size of solder contact area, and its target location, and the actual location and size of the solder contact area, the user can determine whether adjustment is required. If adjustment is required, the software will be able to determine it based on the acquired data, or the user can manually make the adjustment using the video feed and the fixed markers. Preferably though the adjustment parameters will be used to calculate a new, optimal registration location for the soldering nozzle.

The procedure can be repeated for multiple selective soldering locations on the plane of the PCB if the inventive apparatus is incorporated over a PCB workstation within the soldering apparatus. This can then determine if the nozzle registration apparatus under the workstation has step errors, i.e. intended displacements in the X, Y or Z directions are not replicated by the actual displacements.

Figure 2:
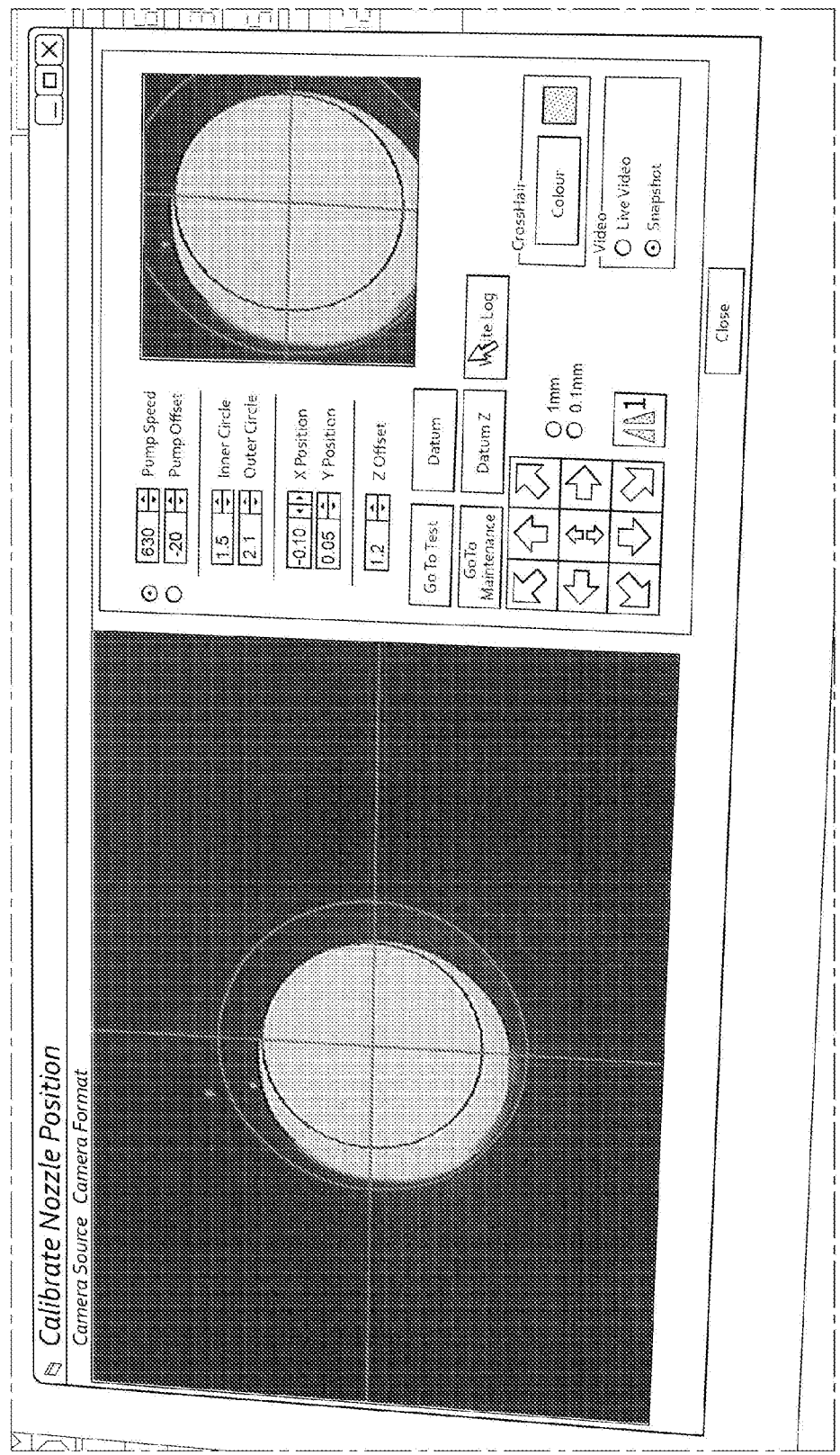
FIG. 2 is a screen shot of a user interface of a program for executing a calibration routine in accordance with FIG. 1, with the user having recorded a first detected position and shape of the solder contact area prior to calibration. Two images are presented—one of the solder flow, and the other being a freeze-frame from that solder flow.

With reference to FIG. 2 of the drawings, there is next represented a screen shot of a user interface of a sample piece of software that implements an embodiment of the invention. The bigger screen is the feed from the camera, which is focussed at the underside of the glass—the user can see the solder flow's contact area through the glass in real time, although the image is frozen at the point at which the nozzle starts to retract back away from the glass so as to secure a fixed image of the contact area for this test run. The smaller image is a freeze frame.

In FIG. 2, the position of the computer's cursor is over the "Write Log" control button, and that button has been "depressed". By doing this a frame of the camera feed is stored in the computer and this is displayed in the (smaller) "frozen" image on the right hand side of the user interface.

The parameters visible just on the left of the frozen image provide the location and size of the inner and outer reference circles. The reference circles, as explained above, represent a target value for the solder contact area, and we can clearly see that the measured solder contact area is off target in so far as its X and Y location is concerned. The size of the contact area, however, is within accepted tolerances, despite it being offset.

Figure 3:
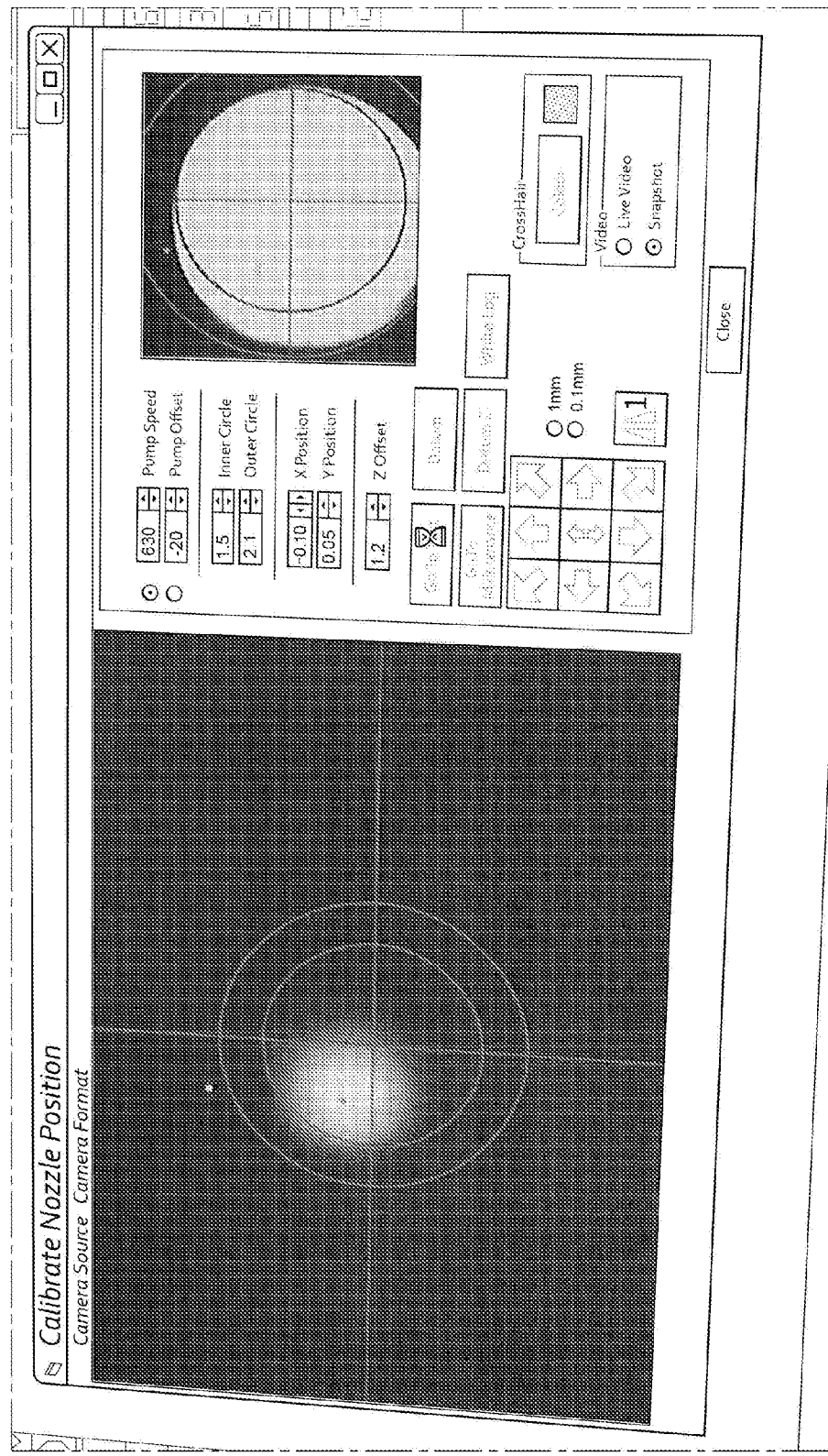
FIG. 3 is a subsequent screen shot, wherein the user has ordered a further test and the nozzle is approaching its preselected registration position by moving from the underside of a sheet of material towards the sheet of material—a movement in the Z direction. Two images are presented—one of the approaching solder flow, and the other being a freeze-frame from FIG. 2.

In FIG. 3, the user has depressed the "Go To Test" control button. When the "Go To Test" control button is depressed, the nozzle is moved from a retracted position vertically towards the glass to a pre-programmed "soldering" position. It is currently approaching the glass, but has not yet contacted the glass, and thus the solder flow is out of focus. The larger image in FIG. 3 is the molten solder bubble while it is still at a distance from the glass, although it is in the process of coming nearer. The smaller frozen image is still the one from FIG. 2.

Figure 4:
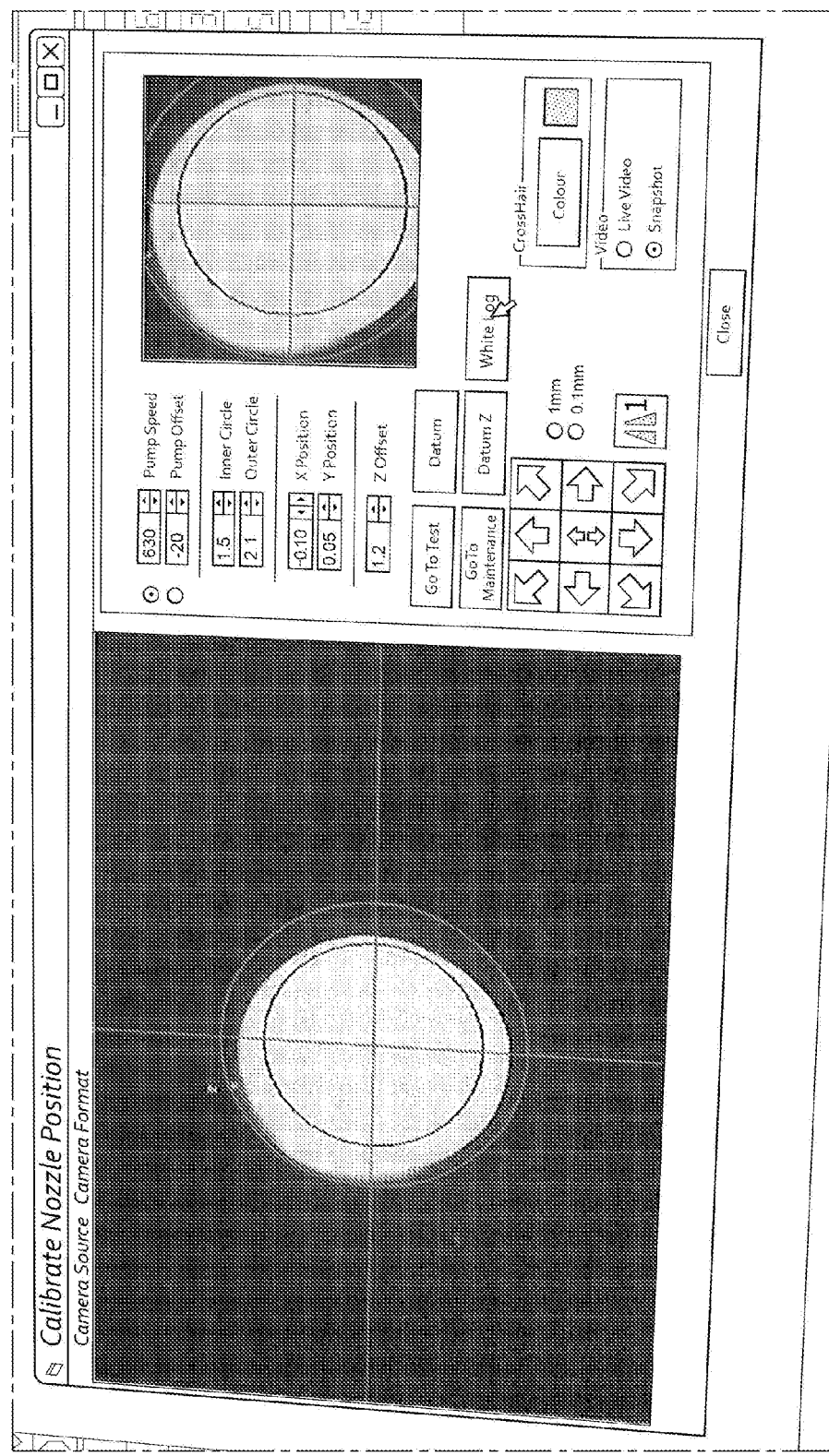
FIG. 4 is a subsequent screen shot, with the user having recorded a second detected position and shape of the solder contact area following a first corrective calibration. Two images are presented—one of the solder flow, and the other being a freeze-frame from that solder flow.

In FIG. 4, the nozzle has arrived at its pre-programmed "soldering" position and the user has again depressed the "Write Log" button to cause a new image to be recorded in the computer. The new image is represented in the smaller screen, and replaces the former image from FIG. 2. We can see that the solder contact area now appears more centred compared to the image from FIG. 2, at lease regarding direction Y. There is still a significant offset along the X direction. Again the size of the bubble seems to be on target, although the shape is offset as noted here above.

Figure 5:
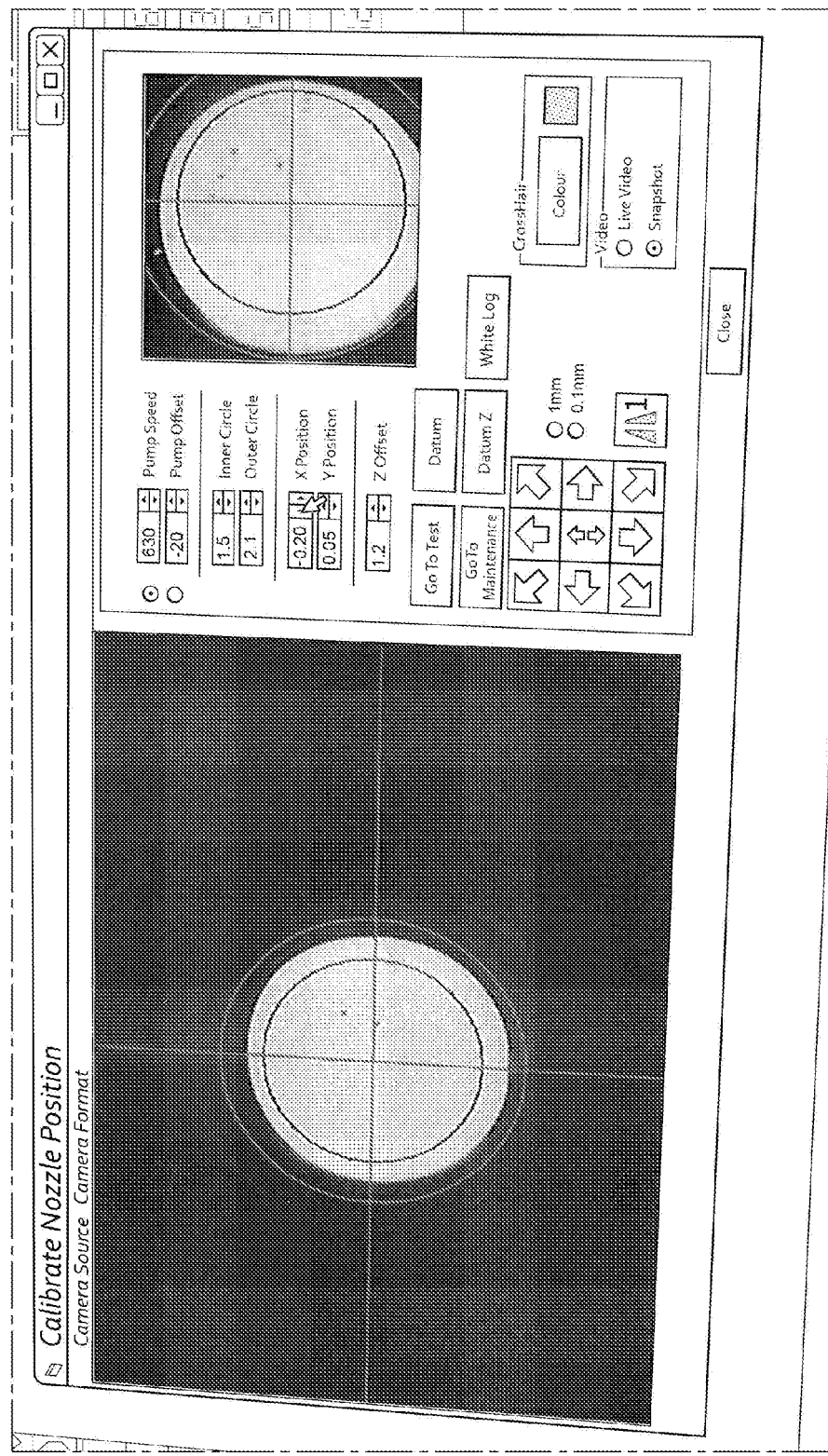
FIG. 5 is a subsequent screen shot, where the user has sufficiently centred the position of the contact area in the X direction. Two images are shown, one of the solder flow, and the other of a previous freeze frame prior to the centring correction having been made.

FIG. 5, the user has decided to interact with the X position of the solder contact area to apply a compensation or correction (see the position of the cursor in FIG. 5—it is changing the X position), and this has centred the solder contact area as desired, as is displayed on the larger camera feed screen of FIG. 5. On the smaller screen, the image is still that of FIG. 4.

The comparison between the centred shape on the bigger screen of FIG. 5, and the offset shape on the smaller screen is clear. The user will then store the frame now displayed on the larger screen by writing the log again with the "Write Log" button. The applied adjustment is thus stored in readiness for deployment during soldering operations, or for a rerun of the test procedure.

Figure 6:
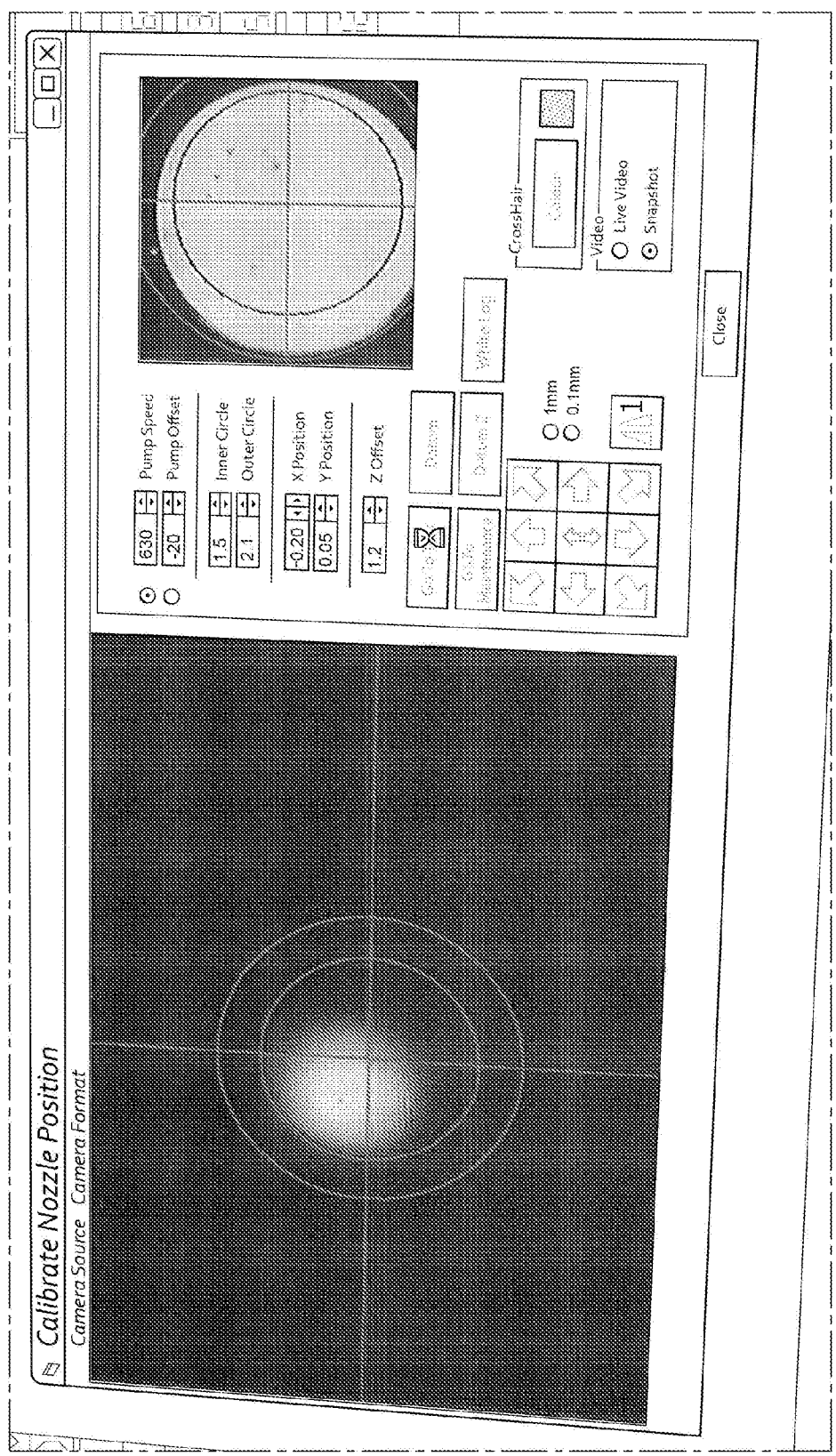
FIG. 6 is a further screen shot, wherein the user has ordered a further test after the centring of the contact area in the X direction, with the nozzle approaching its new registration position in the Z direction.

In FIG. 6, the user has just depressed the "Go To Test" button, and a similar procedure as the one illustrated in FIG. 3 is followed by the software. This may be to verify the accuracy of the contact area after a number of soldering cycles. As can be seen the stored image shows a bit of an off set so this is a second cycle to determine average contact areas. Since it is offset, there may be wear on the nozzle. It could be corrected, but a replacement nozzle may alternatively be fitted.

Figure 7:
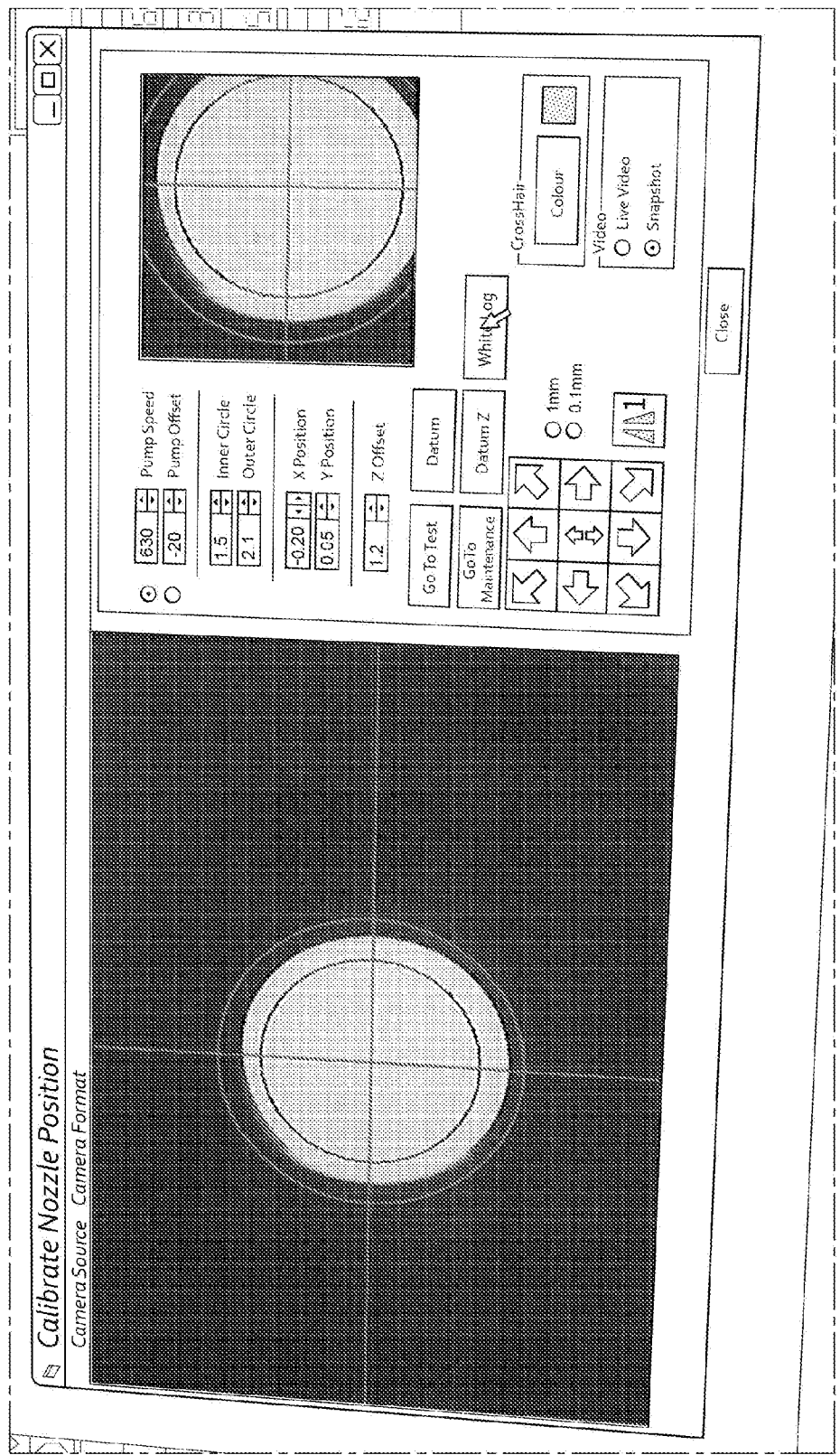
FIG. 7 is a further screen shot, with the user about to record a third detected position and shape of the solder contact area prior to further calibration.

In FIG. 7, a replacement nozzle is now resulting in a centred contact area, as per the live feed in FIG. 5. The user can see that the X adjustment previously applied appears still to be working—the solder contact area now appears to be acceptably centred and furthermore its shape seems to be within target. The user, therefore, has already decided to save the test to the computer by depressing the "Write Log" control button, so the still image corresponds to the live feed.

Figure 8:
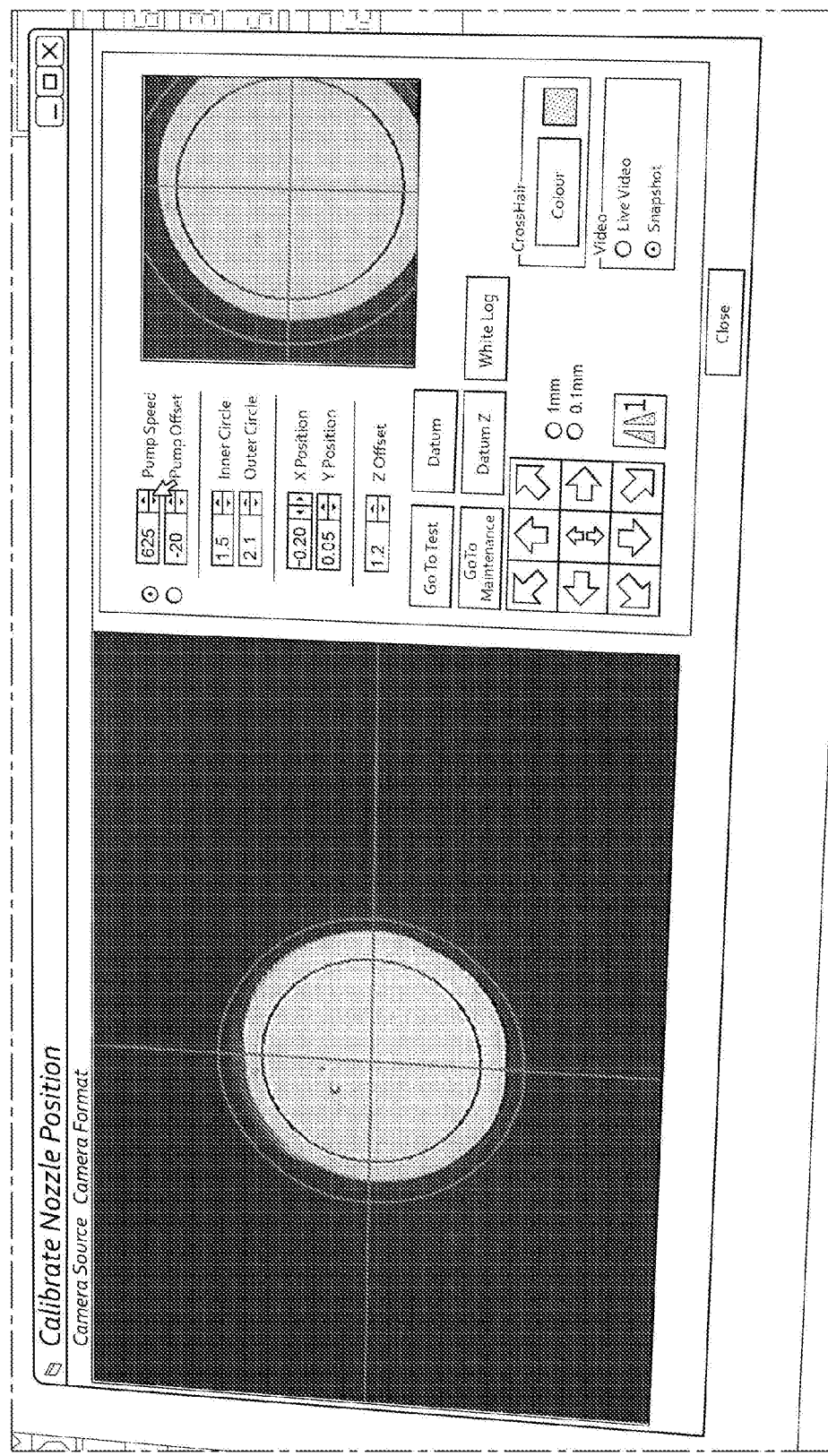
FIG. 8 is a further screen shot, with the user about to calibrate the size of the solder contact area by intervening on the solder pump speed.

In FIG. 8, the user has operated the "Pump Speed" control of the user interface. This can be used to correct or alter the shape and size of the solder contact area. By decreasing the pump speed, the user expects to see a decreasing size of contact area, and it may also be to correct an occurrence of jetting.

Figure 9:
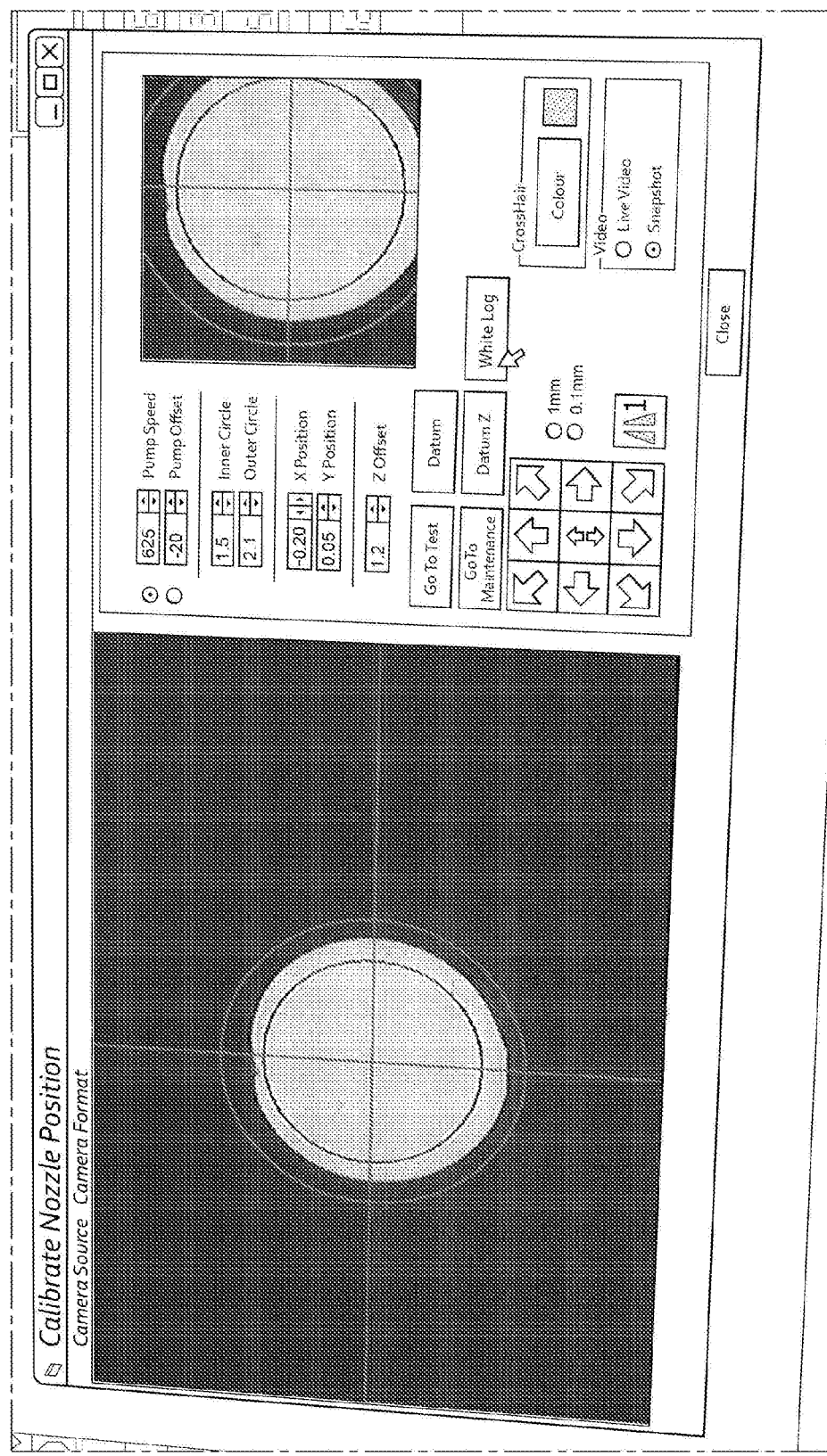
FIG. 9 is a further screen shot, with the user about to record a fourth detected position and shape of the solder contact area prior to further calibration.

FIG. 9 shows a slightly reduced size of solder contact area compared to FIG. 8 since the pump speed has been brought down slightly by the user from a value of 630 to 625. The user records the test, and as usual the frame is saved in the computer and displayed on the smaller screen of FIG. 9.

Figure 10:
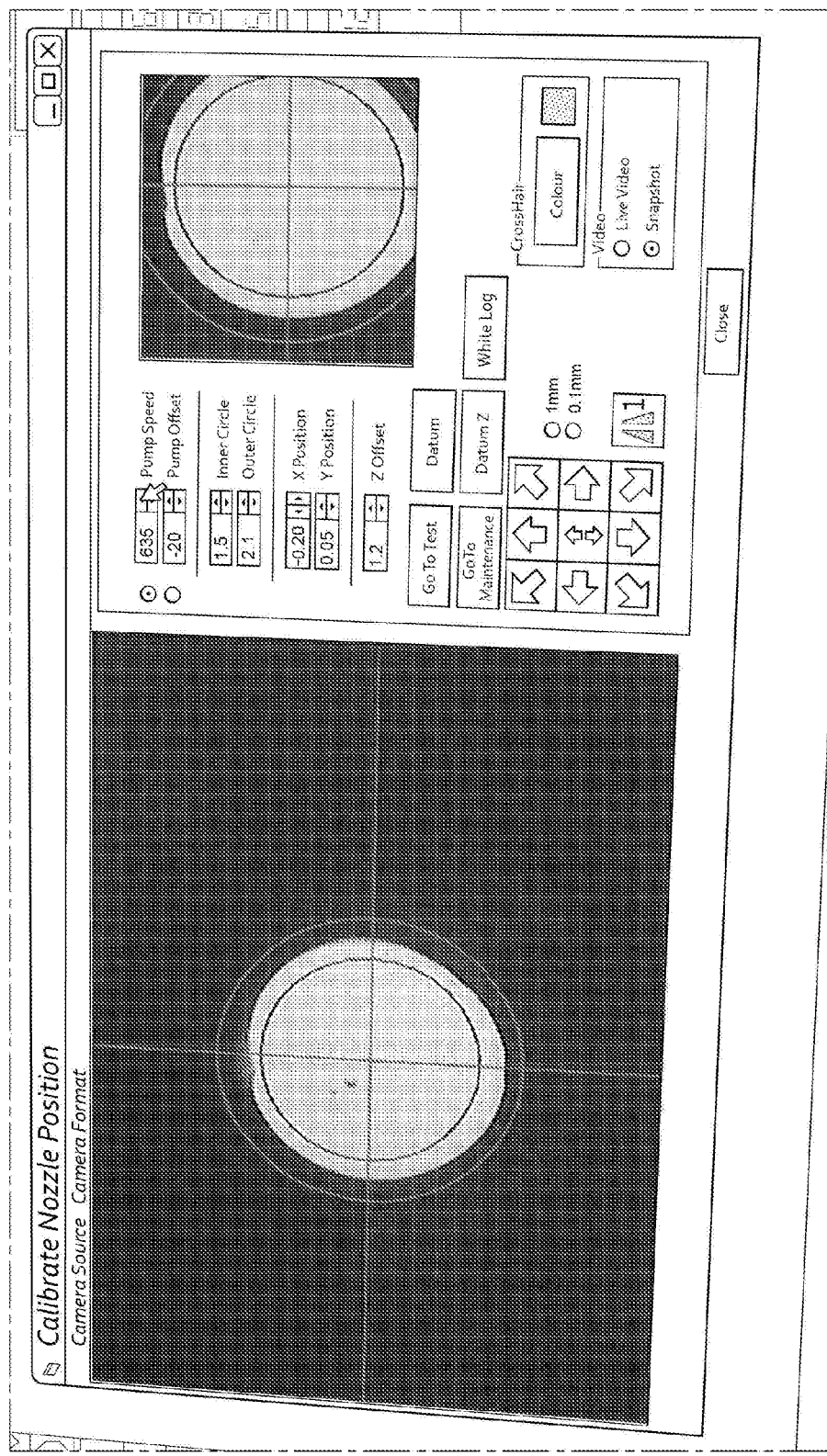
FIG. 10 is a further screen shot, with the user about to calibrate the size of the solder contact area by intervening further on the solder pump speed.

In FIG. 10, the user has again changed the solder flow by slightly increasing the pump speed to 635. As can be seen, the image on the big screen has clouding at the top edge, possibly suggesting a problem with the nozzle. FIG. 8 likewise showed it, and it was less noticeable in FIG. 9, but it is insufficiently bad to fall outside acceptable parameters.

Repeated tests can offer a means of characterising the reproducibility of the solder shape and location for given X, Y and Z coordinates, all the other parameters being the same. This is useful for soldering nozzle testing and characterisation application.

The invention provides a mechanism for allowing rapid, determinable control over the size of the contact interface between the solder flow and the object to the soldered, i.e., typically, terminations of components placed on PCB tracks in selective soldering applications. Consequently, selective soldering can be performed at higher precision and accuracy.

Also, as certain selective soldering applications move towards the use of nozzle tips of a very small size (e.g. with solder outlets as small as 1.5 mm), the size of the solder contact area can become a parameter that is increasingly difficult or important to control. The invention encompasses a methodology for improving or facilitating that control, and for allowing the general and rapid characterisation and calibration of soldering nozzles in use (i.e. while solder flows).

In addition to the calibration processes for the contact area, the present invention also provides systems for checking the alignment of the nozzle against the underside of the PCB, e.g. upon traversing the nozzle back into the workstation for the PCB, when guided by the nozzle's camera. There is a possibility of x, y and z variations between the park area, or the location at which the contact area is aligned, and the underside of a PCB (once located in the PCB workstation), and all three need to be correctly controlled or applied by the nozzle's carriage control. Further, setting these parameters at the park station (e.g. using the sheet of glass) is potentially inadequate or unreliable when using a different camera for guidance at the underside of the PCB. Therefore, checking the alignment of the application of the solder bubble to the intended location of a PCB is an important additional calibration stage and may well be carried out every four hours or so, e.g. by a manual check or by an automated system, so as to ensure ongoing accurate soldering practices.

Yet further, the present invention provides an initial set up process for a nozzle that can be undertaken for additionally providing a datum level for the PCB workstation relative to the park station. That datum level can then be incorporated into the nozzle movement control software so as to correct for discrepencies between the level of the top of the nozzle when changing nozzles, and further to determine any step change in the z axis between the expected locus of the underside of the PCB and the expected locus of the underside of the sheet of material/glass (e.g. at the park station).

These two additional features will now be described in further detail below with reference to FIGS. 14 to 16 and 11 to 13 respectively FIGS. 11 to 13 show a device used for obtaining a manual datum level for the soldering nozzle with respect to an underside of a PCB workstation. As shown there is a plate 10 on which is located a holder 12 for holding a DTI clock 14 (see e.g. the clock of FIG. 12).

DTI clocks are well known in mechanical arts for measuring small distances very accurately. The example shown in FIG. 12 has a tip 16 at its bottom end which can slide relative to a housing 18 for moving a needle on the face 20 of the clock 14, thus providing am accurate displacement measurement for the tip relative to the housing. The DTI clock 14 is mounted in the holder 12, e.g. as shown in FIG. 13, with the tip 16 descending below the bottom surface of the plate 10. This plate and clock arrangement is of a fixed configuration whereby the locus of the tip of the DTI clock below the underside of the plate 10 is fixed, and thus the needle on the clock can provide a reading of displacement and thus a distance of the nozzle from the underside of the plate, that underside being a good approximation of the location of an underside of a PCB once the PCB is located instead in the PCB workstation.

The tip 16 of the clock extends underneath the plate 10 such that it has a resemblance to a leg of a component on a PCB that is to be soldered to the track on the PCB. It could be flush, but in practice the nozzle would never be intended to hit the underside of a PCB so extending the leg below the underside of the plate 10 ensures a contact can be achieved between the tip of the leg and the tip of the nozzle.

To take a nozzle positional reading, the tip of a nozzle on the soldering apparatus' nozzle carriage is moved underneath the plate 10 once that plate has been correctly positioned and mounted in the PCB workstation. This is generally done without commencing the flow of solder, i.e. while the solder pump is disengaged. That nozzle is then engaged with the tip of the clock so that a reading can be taken on the face of the clock, which measurement can then be used by nozzle's control system to determine where the nozzle's tip is with respect to the underside of the plate (and thus the underside of a PCB when undertaking soldering operations).

The nozzle's control system, which controls the mechanisms for moving a carriage for the nozzle, thus has an accurate Z axis measurement for the new nozzle.

This process is carried out under the guidance of an image feed from a camera on the carriage—which camera feed shows a target for the nozzle. See, for example, FIG. 16, where the cross-hairs are targeting the intended target for the nozzle (in this case nothing since the plate is not present and the soldering apparatus is open). The nozzle thus can nevertheless be manually or automatically guided into its contact with the tip of the clock. The accuracy of the actual engagement, however, is incidental—the reading on the clock provides an accurate measurement of the actual position/displacement of the tip of the clock so the degree of engagement of the tip of the clock (which varies due to inaccuracies in the guidance) does not vary the accuracy of the datum reading (since it is corrected by the reading on the clock).

This guidance may be manual or automated. Likewise the clock reading can be captured manually or automatically.

This z axis determination is an important calibration since it is important to know when the nozzle would contact the underside of the plate since the length of the legs of components extending through a PCB will be known in advance and it is important for the nozzle never to touch them. Thus, a positioning of the nozzle under the PCB when it replaces the plate can be controlled with this datum reading by the control system automatically. This is to avoid the nozzle ever touching the legs of the components—such touching could misalign the component, after all.

In addition, the z axis reading can be used to determine any step change between the height of the underside of the plate and the underside of the sheet of material e.g. at the park position. After all, using the camera on the carriage, the nozzle can be guided also to the sheet of material, and when the solder is flowing the point of contact of the solder flow with the sheet of material can be detected. This provides a sufficient indication or reference point for the height of the nozzle relative to the underside of the sheet of material to ensure that the nozzle is never lifted into engagement of the sheet of material (which action would potentially break that sheet of material.

In addition to the z axis reading, the initial contact with the tip of the clock will also allow an x and y axis reading to be taken, and since the relative position of the tip of the clock is also known in the x and y axis relative to the edges of the plate 10, this enables an approximate calibration in the x and y axis for the new nozzle. Further, additional calibrations can occur by rotating the position of the tip 16 into the opposite corner of the PCB workstation, such as by rotating the plate through the horizontal plane through 180° and a further x and y measurement can be taken. This additionally helps the control system to learn how to position the nozzle under the plate 10, e.g. across a greater extent of the PCB workstation.

Although this simple calibration is not particularly accurate at this stage, it is sufficiently accurate to allow a rough approximation of locus of the nozzle tip to be determined. The third aspect of this invention, however, looks to better calibrate the x and y axis measurements—something usefully done after the contact area has been optimised, rather than at this initial calibration stage. During the optimisation of the contact area, however, a comparison of the z, x and y coordinates relative to the known position of the glass or the markers thereon, can be done to gain a fixed positional reference between the two cameras. This can then be further corrected once the next calibration is done. After all, displacements by the carriage are computer controlled and thus are known as a function of the step motor control.

Figure 14:
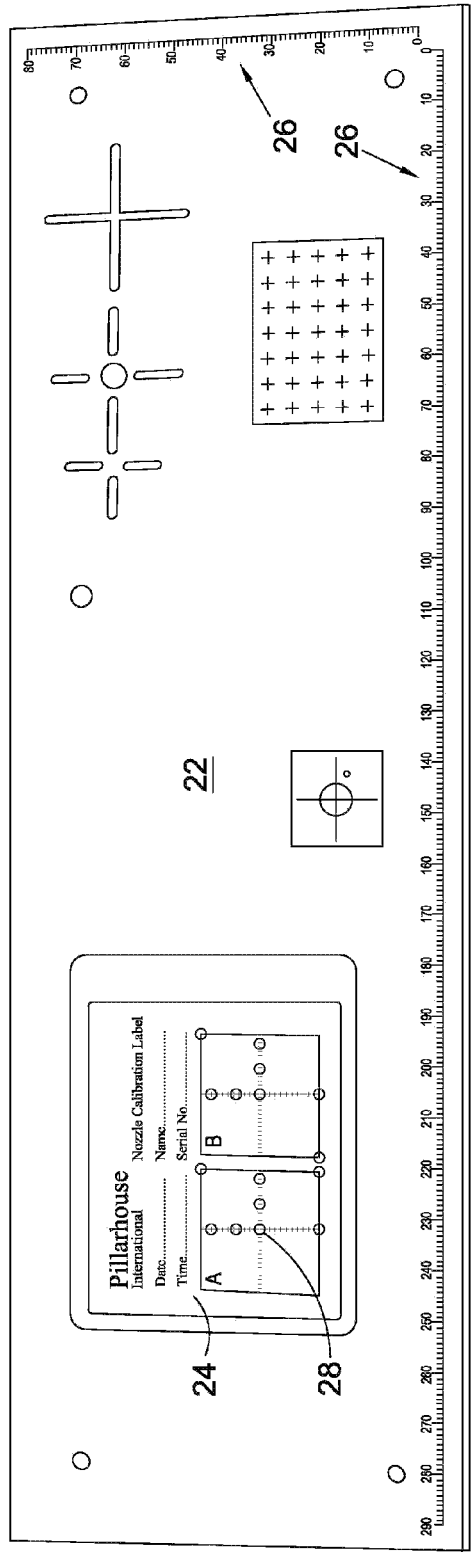
FIG. 14 shows a dedicated test plate for checking the calibration of the camera-guided control of the carriage in the PCB workspace.
Figure 15:
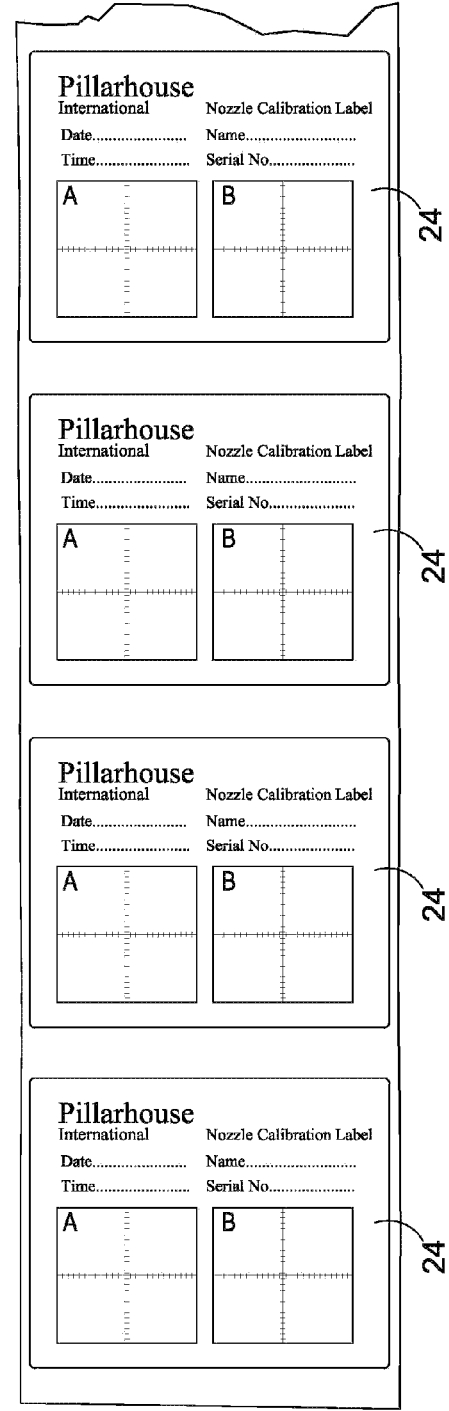
FIG. 15 shows a strip of thermal paper for use as a test paper in checking the calibration.

The checking of the calibration of the camera-guided control of the carriage in the PCB workspace will now be described with reference to FIGS. 14 to 16.

This final calibration process is again carried out using the camera on the nozzle carriage of the soldering apparatus. It is also carried out using a dedicated test plate 22, although it may be incorporated onto the plate that carries the clock.

The test plate 22 has various markings thereon, including measurement markers 26 that can be used to calibrate the carriage control with respect to deltas along the x and y axes (i.e. movements, rather than absolute positions) and a test paper, preferably in the form of a sticker 24, that is preferably made from a thermal paper such as fax paper, which test paper is marked by contact thereof by flowing solder. Thermal paper is particularly suited since it is marked by heating, and flowing solder is at a suitable temperature to achieve such heating, and since it can be supplied on a roll, as per the strip in FIG. 15.

Figure 16:
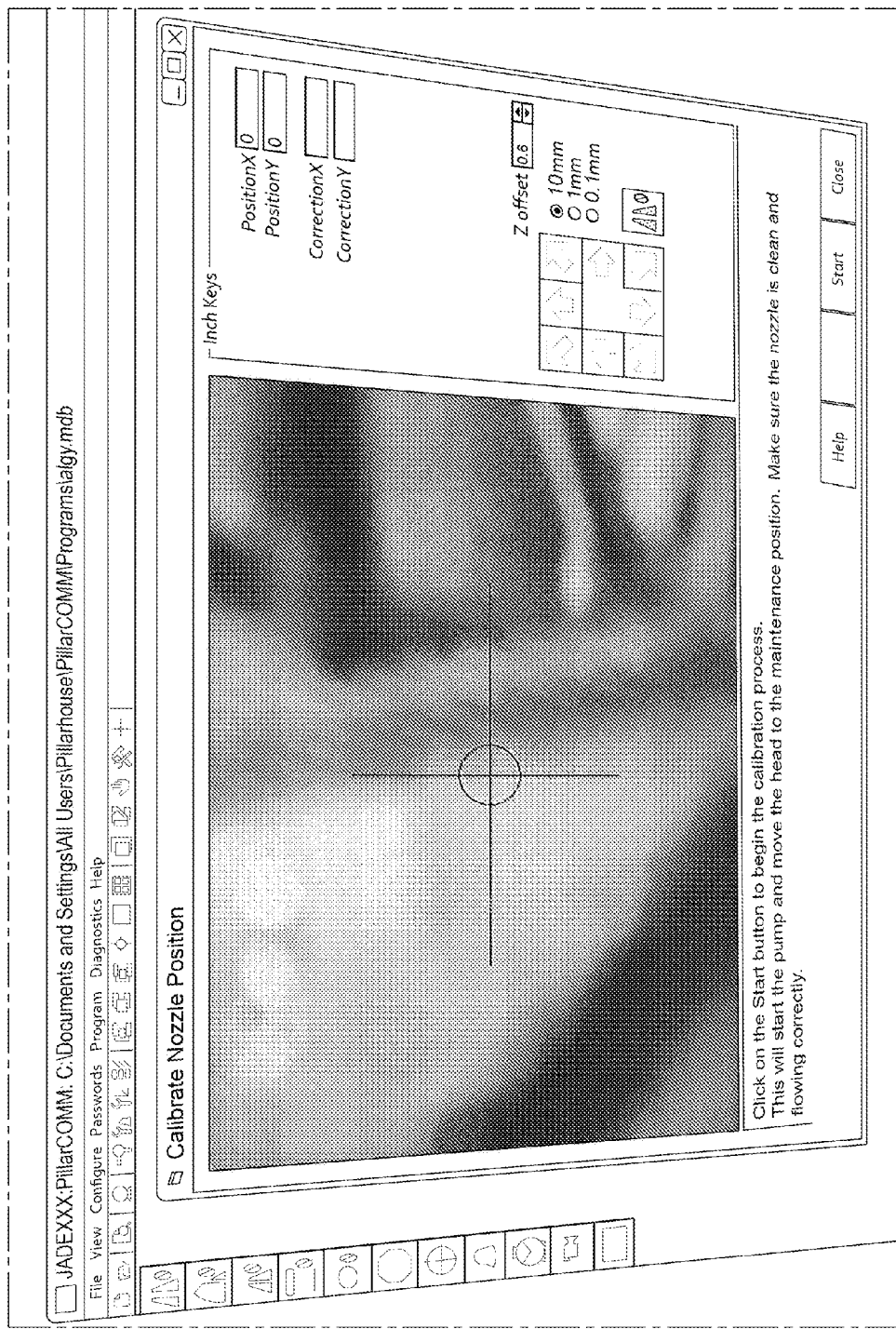
FIG. 16 shows a camera view of a camera used in checking the calibration.

FIG. 16 shows the camera view for the second camera. In use it looks upwards from the carriage towards the PCB (or underside of the text plate) and thus can look for areas of the test plate 22, and target them with the nozzle. Having a wide field of view, the same camera might also target items for fluxing, but different cross hairs would be used for that.

Upon the nozzle, and more specifically the solder flow therefrom touching the test paper, a mark 28 is printed onto the paper 24. Further, by use of x/y axis control, more than one such mark may be made—in this case there are eight on the first test graph A—the one to the left side of the test paper 24. Since the test paper is in accurate registration on the test plate 22, by having the solder flow engage at intended pre-programmed positions, or desired test positions, on the test plate 22, the accuracy of the carriage control can be verified by using the graduations on the test graph A. If accurate, the x/y control axes are calibrated correctly, but if not they can be corrected and a further test can be carried out on graph B (to the right of the test paper 24). Here a further eight test marks are shown, although the final one was to an opposing corner of the graph.

The calibration in the X and Y axes can thus be confirmed, and this can also allow the relative position of the second camera at the park station to be calibrated too with respect to the carriage's control system (and its camera).

Additionally, the correct size for the contact area can also be checked, and any necessary adjustments can again be made, although this is unlikely to be necessary since it was already checked in a previous step.

Although the various aspects of the present invention have been described with reference to the solder nozzle, these approaches may also be useable for calibrating, at least in part, the position of the fluxer (for which a third camera might be provided, if the carriage's first camera is not given a suitable field of view).

The present invention has been described above purely by way of example. Modifications in detail are possible, as it will be appreciated by the skilled person, within the scope of the disclosure herein, and particularly with regard to the appended claims.

The invention claimed is:

1. A method of observing, determining or measuring a parameter of a contact area produced between a flow of solder ejected from a soldering nozzle and a surface, the method comprising the steps of:
   providing the surface on a sheet of material through which the contact area can be visually detected;
   flowing the solder through the soldering nozzle;
   bringing the flow of solder into contact with the surface, thereby creating the contact area between the flow of solder and said surface;
   observing the contact area from a side of the sheet of material opposite to the contact area;
   measuring one or more parameter of said contact area;
   comparing said one or more parameter against a stored value, or a desired value, or threshold values, whereby deviations therefrom can be detected or determined;
   wherein when a deviation is detected or determined, or when the deviation exceeds a given threshold, the method then involves attempting to correct the deviation or defect; and
   wherein when, from the observed contact area, it is determined that the deviations cannot be corrected, it is determined that the nozzle has failed or is otherwise damaged, and a warning is provided to a user or operator.

2. The method of claim 1, wherein a measured parameter is one or more of a size or length, e.g. the splash-length or splash-width or splash-diameter, a position of the splash relative to a predetermined marker, or a shape of the splash.

3. The method of claim 1, wherein relative positions of the nozzle or sheet are adjusted.

4. A method according to claim 1, wherein the nozzle position can be adjusted by raising or lowering the nozzle respectively to increase or reduce the size of the contact area.

5. A method according to claim 1, wherein the parameter is measured relative to one or more markers on the sheet.

6. The method of claim 5, wherein those markers define optimal splash positions or optimal splash shapes or optimized splash sizes, or threshold values therefor.

7. A method according to claim 1, wherein if from the observed contact area it is determined that the nozzle may be exhibiting the characteristics of dewetting, freezing, jetting or bobbling, it is determined that the nozzle or soldering apparatus has failed or is otherwise damaged.

8. A method according to claim 1, wherein the solder is illuminated to assist the observation of the contact area.

9. A method according to claim 1 wherein the contact area is magnified to assist the observation of the contact area.

10. A method according to claim 1, wherein an image of the contact area is captured by a camera.

11. The method of claim 10, wherein the camera is located above the sheet of material.

12. A method of assessing for any discrepancy between a target value and a measured value of a parameter of a contact area produced between a flow of solder ejected from a soldering nozzle and a surface, the method comprising the steps of:
   (i) measuring a value of the parameter of the contact area produced between the flow of solder ejected from the soldering nozzle and the surface using a method comprising the steps of:
   providing the surface on a sheet of material through which the contact area can be visually detected;
   flowing the solder through the soldering nozzle;
   bringing the flow of solder into contact with the surface, thereby creating the contact area between the flow of solder and said surface;
   observing the contact area from a side of the sheet of material opposite to the contact area; and
   measuring one or more parameters of said contact area;
   (ii) assessing for any discrepancy between the target value and the measured value; and
   (iii) when a discrepancy is detected or determined, or when the discrepancy exceeds a given threshold, attempting to correct the deviation or defect, and when, from the observed contact area, it is determined that the discrepancies cannot be corrected, it is determined that the nozzle has failed or is otherwise damaged, and a warning is provided to a user or operator.

13. A method of calibrating a contact area produced between a flow of solder ejected from a soldering nozzle and a surface, the method comprising the steps of:

assessing for any discrepancy between a target value and a measured value of a parameter of a contact area produced between a flow of solder ejected from a soldering nozzle and a surface using the method of claim 12; and reducing said discrepancy by one or more of the following actions:

changing the speed of a solder pump;

adjusting the relative location of the solder nozzle in an X direction;

adjusting the relative location of the solder nozzle in a Y direction; and adjusting the relative location of the solder nozzle in a Z direction;

wherein the X direction and the Y direction are defined by an X-Y plane parallel to the plane of the sheet of material, and the Z direction is orthogonal to the X-Y plane.

* * * * *